United States Patent
Bomkamp

(10) Patent No.: US 9,969,673 B2
(45) Date of Patent: May 15, 2018

(54) PROCESS FOR THE MANUFACTURE OF 1,1'-DIFLUOROSUBSTITUTED DIALKYL CARBONATES, ISOMERS THEREOF AND ELECTROLYTE COMPOSITIONS CONTAINING THEM

(71) Applicant: SOLVAY SA, Brussels (BE)

(72) Inventor: Martin Bomkamp, Hannover (DE)

(73) Assignee: SOLVAY S.A., Brussels (BE)

( * ) Notice: Subject to any disclaimer, the term of this patent is extended or adjusted under 35 U.S.C. 154(b) by 786 days.

(21) Appl. No.: 14/362,624

(22) PCT Filed: Nov. 23, 2012

(86) PCT No.: PCT/EP2012/073485
§ 371 (c)(1),
(2) Date: Jun. 4, 2014

(87) PCT Pub. No.: WO2013/083418
PCT Pub. Date: Jun. 13, 2013

(65) Prior Publication Data
US 2014/0342221 A1   Nov. 20, 2014

(30) Foreign Application Priority Data
Dec. 7, 2011   (EP) .................................... 11192446

(51) Int. Cl.
| | | |
|---|---|---|
| C07C 68/02 | (2006.01) | |
| C07C 69/96 | (2006.01) | |
| H01M 10/0525 | (2010.01) | |
| H01M 10/0567 | (2010.01) | |
| H01M 10/0569 | (2010.01) | |
| H01M 10/052 | (2010.01) | |

(52) U.S. Cl.
CPC .............. *C07C 68/02* (2013.01); *C07C 69/96* (2013.01); *H01M 10/0525* (2013.01); *H01M 10/0567* (2013.01); *H01M 10/0569* (2013.01); *H01M 10/052* (2013.01); *H01M 2300/0025* (2013.01); *H01M 2300/0037* (2013.01)

(58) Field of Classification Search
CPC ...... C07C 68/02; C07C 69/96; H01M 10/052; H01M 10/0525; H01M 10/0567; H01M 10/0569; H01M 2300/0025; H01M 2300/0037
See application file for complete search history.

(56) References Cited

U.S. PATENT DOCUMENTS

| | | |
|---|---|---|
| 3,213,062 A | 10/1965 | Ellingboe et al. |
| 5,712,407 A | 1/1998 | Kreutzberger et al. |
| 5,916,708 A | 6/1999 | Besenhard et al. |
| 6,159,640 A | 12/2000 | Appel et al. |
| 6,489,064 B2 | 12/2002 | Appel et al. |
| 6,677,085 B2 | 1/2004 | Appel et al. |
| 2009/0253044 A1 | 10/2009 | Nogi et al. |
| 2011/0159382 A1 | 6/2011 | Matsui et al. |

FOREIGN PATENT DOCUMENTS

| | | |
|---|---|---|
| EP | 0249556 | * 12/1987 |
| EP | 0249556 A1 | 12/1987 |
| JP | 2004010491 A | 1/2004 |
| JP | 2006001843 A | 1/2006 |
| WO | 2007042471 A1 | 4/2007 |
| WO | 2011006822 A1 | 1/2011 |
| WO | 2011036293 A2 | 3/2011 |

OTHER PUBLICATIONS

English translation of EP Publication 0249556, Dec. 1987.*
M. Hasegawa et al., "Regioselective Anodic Monofluorination of Ethers, Lactones, Carbonates, and Esters Using Ionic Liquid Fluprode Salts", J. Electrochem. Soc. vol. 153, No. 10, 2006, pp. D 162-D166.

* cited by examiner

*Primary Examiner* — Brittany Raymond

(57) ABSTRACT

Fluoroalkyl alkyl carbonates which are suitable as additives or solvents in lithium ion batteries are prepared from fluoroalkyl fluoroformiates and an aldehyde, preferably formaldehyde and acetaldehyde. 1,1'-difluoromethyl carbonate and 1,1'-di-fluorodiethylcarbonate are the preferred compounds prepared by the process of the present invention.

11 Claims, No Drawings

PROCESS FOR THE MANUFACTURE OF 1, 1'-DIFLUOROSUBSTITUTED DIALKYL CARBONATES, ISOMERS THEREOF AND ELECTROLYTE COMPOSITIONS CONTAINING THEM

This application is a U.S. national stage entry under 35 U.S.C. § 371 of International Application No. PCT/EP2012/073485 filed Nov. 23, 2012, which claims priority to European Patent Application 11192446.0 filed on 7 Dec. 2011. The entire contents of these applications are explicitly incorporated herein by this reference.

The present invention concerns a process for the preparation of 1,1'-difluorosubstituted dialkyl carbonates, novel 1,1'-difluorodialkyl carbonates.

Fluoroalkyl alkyl carbonates, e.g. fluoromethyl methyl carbonate, are known solvent additives for lithium ion batteries. The latter compound can be prepared by the reaction of dimethyl carbonate and elemental fluorine, as described in JP patent application 2004010491, or by electrochemical fluorination, see JP2006001843. Difluorinated products—difluoromethyl methyl carbonate and bis-fluoromethyl carbonate—and higher fluorinated products reduce yield and make separation processes necessary.

WO 2011006822 discloses the manufacture of 1-fluoroalkyl(fluoro)alkyl carbonates.

M. Hasegawa, H. Ishii, Y. Cao and T. Fuchigami describe in J. Electrochem. Soc. 153 (10), D162-D166 (2006) the manufacture of bis-(1-fluoroethyl) carbonate, probably a side product in a process comprising the anodic fluorination of diethyl carbonate.

Among others, an object of the present invention is to provide a process which allows the selective manufacture of 1,1'-difluorinated dialkyl carbonates. This object and other objects are achieved by the invention as outlined in the description and the claims.

The process according to the present invention provides for the manufacture of 1,1'-difluorodialkyl carbonates of the general formula (I), $R^1CHF$—OC(O)—$OCHFR^2$, wherein $R^1$ and $R^2$ are the same or different and denote H or linear or branched alkyl with 1 to 3 C atoms, comprises a step of reacting a fluoroalkyl fluoroformiate of formula (II), $R^1CHFOC(O)F$, wherein $R^1$ has the meaning given above, with an aldehyde of formula (III), $R^2$—CH(O), wherein $R^2$ has the meaning given above, or a respective trimer.

For the sake of simplicity, the compounds of formula (II) will be denoted below simply as "fluoroformiates".

Preferably, $R^1$ is H or $CH_3$. Preferably, $R^2$ is H or $CH_3$. Preferably, 1,1'-difluorodimethyl carbonate or 1,1'-difluorodiethyl carbonate are produced.

The molar ratio between the fluoroformiate of formula (II) and the aldehyde of formula (III) preferably is equal to or greater than 0.3:1, more preferably, it is equal to or greater than 0.9:1. Preferably, it is equal to or lower than 5:1, more preferably, it is equal to or lower than 3:1. Very good results are achieved when the ratio of fluoroformiate and aldehyde is in the range from 0.95:1 to 1.05:1.

The temperature during the reaction between fluoroformiate and aldehyde is not critical. Generally, cooling is not necessary, but if for specific reactants, the reaction should be exothermic, it may be advisable to cool the reaction mixture. The temperature during the reaction is preferably equal to or higher than −80° C., more preferably, equal to or higher than −78° C. Preferably, the temperature is equal to or higher than 0° C., more preferably, equal to or higher than 20° C.

The upper limit of the reaction temperature can be dependent from pressure and boiling point of the starting materials, e.g. from the boiling point of the alcohol. Often, the temperature is equal to or lower than 150° C., more preferably, equal to or lower than 85° C., especially preferably, equal to or lower than 50° C. A preferred range is from 0 to 150° C., more preferably, from 20 to 50° C.

The reaction is preferably performed in the presence of an acylation catalyst. Without being bound by any theory, it is assumed that the activation catalyst serves to transform the 1-fluoroalkyl fluoroformiate of formula (II) into a kind of "activated ester" by substituting the F— anion from the C(O)F group; the F— anion is assumed to react with the aldehyde of formula (III) thereby forming a fluoroalcoholate. The "activated ester" is considered to be more reactive than the 1-fluoroalkyl fluoroformiate itself, and it is assumed that it reacts with the fluoroalcoholate to provide the 1,1'-difluorodialkyl carbonate of formula (I).

A preferred type of acylation catalysts are aromatic compounds having at least one N atom in the aromatic ring. Pyridine and substituted pyridine compounds are especially suitable as catalysts. Pyridine substituted by electron donating groups, especially pyridine substituted by at least one amino group, is highly suitable. Dialkylaminopyridines, and notably 4-dialkylaminopyridines, are especially suitable as acylation catalysts. The term "alkyl" preferably denotes C1 to C4 alkyl, especially methyl, ethyl, isopropyl and n-propyl. 4-dimethylaminopyridine ("DMAP") is especially preferred. The following reaction scheme is intended to give an explanation of the reaction:

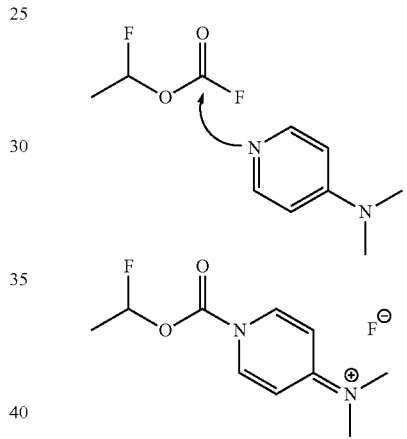

The drawing on the left shows the starting compounds, namely the 1-fluoroalkyl fluoroformiate and the DMAP molecule. The "activated ester" is shown on the right.

The F— anion and the aldehyde form the fluoroalcoholate which reacts with the "activated ester" forming the 1,1'-difluorodialkyl carbonate while the DMAP is split off from the activated ester:

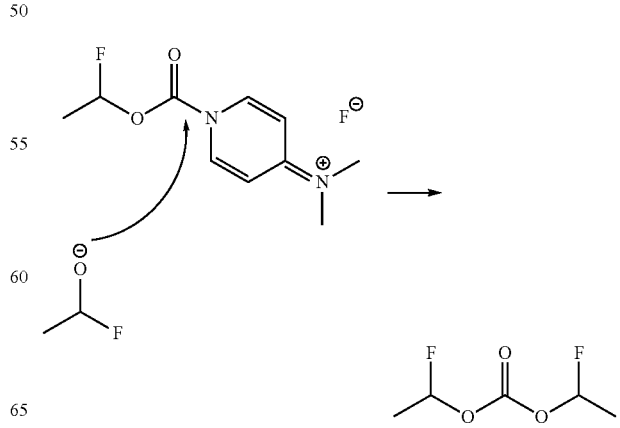

As mentioned above, the reaction scheme given above reflects only a theory and is not intended to limit the invention.

The reaction can be performed in any suitable reactor, e.g. in an autoclave.

The reaction can be performed batch wise or continuously.

Preferably, the reaction is performed without additional applying pressure. This means that the reaction is preferably performed under autogenous pressure or at ambient pressure. But if desired, the reaction can be performed at reduced pressure or at a pressure greater than ambient pressure, e.g. at a pressure which ranges from equal to or greater than ambient pressure to equal to or lower than 30 bar (abs) or even more.

The reaction can be performed in the absence or in the presence of a solvent. If the reaction is performed in a solvent, preferably at least one aprotic polar solvent is used. Suitable solvents are, for example, ethers, e.g. diethyl ether, esters, e.g. alkyl esters of acetic acid or glycol dialkylesters; preferably, the term "alkyl" denotes here methyl, ethyl or propyl. Organic carbonates are also suitable solvents. Linear dialkyl carbonates can be applied; the alkyl groups may be the same or different, and methyl, ethyl and propyl are preferred alkyl groups. Cyclic carbonates can also be applied as solvent; ethylene carbonate, propylene carbonate and 3,4-dimethyl ethylene carbonates are preferred.

Preferably, the reaction is performed in the absence of a solvent.

The resulting reaction mixture can be separated by known methods, e.g. by distillation, precipitation and/or crystallization. If desired, the reaction mixture can be contacted with water to remove water-soluble constituents. The 1,1'-difluorodialkyl carbonate of formula (I) may be purified in methods known in the art, e.g. by distillation.

1-fluoroalkyl fluoroformiates of formula (II) may be available commercially. They may be prepared from easily available starting compounds. In the following, some methods will be explained in detail how to produce 1-fluoroalkyl fluoroformiates of formula (II).

Compounds of formula (II), $R^1CHFOC(O)F$, can for example be prepared from the respective chloroalkyl chloroformiates in a "Halex" type reaction, i.e. substitution of fluorine atoms for the chlorine atoms by fluorinating agents, as already described above, e.g. using a fluorinating reactant like alkali or alkaline earth metal fluorides, e.g. LiF, KF, CsF, NaF, $NH_4F$ or amine hydrofluorides, or the respective HF adducts. The chloroalkyl chloroformiates themselves are available through the reaction between phosgene and an aldehyde as described in U.S. Pat. No. 5,712,407.

It is preferred to produce the intermediate compounds of formula (II), $R^1CHFOC(O)F$, from carbonyl fluoride and an aldehyde having the formula (IV) $R^1CH(O)$; $R^1$ has the meaning given above and is preferably H or $CH_3$. The aldehyde can be can be applied in the form of trimers, e.g. as paraformaldehyde or trioxane, or as polymers; it is preferred that these compounds are cracked, e.g. thermally, to form the monomeric aldehyde.

The molar ratio between carbonyl fluoride and the aldehyde is preferably equal to or greater than 0.9:1. It is preferably equal to or lower than 5:1.

Preferably, the molar ratio between carbonyl fluoride and aldehyde is in the range of 0.5:1 to 1:10. More preferably, the molar ratio between carbonyl fluoride and aldehyde is in the range of 1:2 to 1:2.5.

Preferably, the reaction between carbonyl fluoride and the aldehyde is catalyzed.

The reaction can be catalyzed, for example, by F—. For example, the reaction can be catalyzed by HF, which may be added as such or prepared in situ by the addition of low amounts of water.

Preferred catalysts are those which contain fluoride anions, e.g. alkaline earth metal fluorides or alkali metal fluorides such as CsF, or catalysts which contain fluoride ions formed from carbonyl fluoride and a pre-catalyst. Preferred pre-catalysts are dialkyl formamides, especially dimethyl formamide. It is assumed that the formamide and carbonyl fluoride form a "naked" fluoride ion which starts a nucleophilic reaction on the aldehyde. The negatively charged oxygen of the formed adduct of the fluoride ion and the aldehyde molecule then reacts with a carbonyl fluoride molecule forming fluoromethyl fluoroformiate or generally, the fluoroalkyl fluoroformiate.

Pyridine, advantageously 4-dialkylaminopyridines, especially 4-dimethylaminopyridine, are also considered as suitable pre-catalysts.

The reaction between $COF_2$ and aldehyde is preferably performed batch wise, e.g. in an autoclave. Alternatively, it can be performed continuously.

The temperature during the reaction of $COF_2$ and aldehyde can vary. For example, when a very effective catalyst is applied, the reaction may even be performed at ambient temperature. It has to be kept in mind, however, that in the case of formaldehyde as starting material, the monomeric form must be provided by cracking of paraformaldehyde or, in case of acetaldehyde, of 1,3,5-trioxane. Thus, while the reaction as such often could be performed at low temperature, nevertheless heat must be applied for cracking if a trimer is introduced into the reaction directly.

In the case of paraformaldehyde as starting material, the reaction preferably is performed at a temperature equal to or higher than 100° C. It is preferably performed at a temperature equal to or lower than 300° C. When aldehydes are used as starting material which must not be thermally cracked, the reaction can be performed at a temperature equal to or higher than 0° C. and equal to or lower than 200° C. It is preferred to perform the reaction at such an elevated temperature and/or for a sufficient time that the desired conversion has taken place.

The reaction between $COF_2$ and the aldehyde of formula (IV) is performed in the liquid phase or under supercritical conditions. The pressure is selected such that at least a part of the carbonyl fluoride is present in the liquid phase.

The pressure depends from the reaction temperature; the higher the reaction temperature, the higher is the pressure in the reactor. The reaction can be performed at ambient pressure (about 1 bar absolute). For example, $COF_2$ can be introduced into the liquid reaction mixture or starting material though an immersed pipe. Preferably, the reaction is performed at a pressure equal to or higher than 5 bar (abs.). Preferably, the reaction is performed at a pressure equal to or lower than 50 bar (abs.). If, as done in one example, the reaction temperature is sufficiently high, the content of the reactor is in a supercritical state. The reaction vessel can be pressurized, if desired, with an inert gas, especially with nitrogen.

If desired, the fluoroformiates, e.g. the fluoromethyl fluoroformiate or fluoromethyl fluoroformiate, can be isolated from the reaction mixture according to methods known in the art, e.g. by distillation. The fluoroformiates are then reacted, as described above, with an aldehyde of formula (III) to produce 1,1'-difluorodialkyl carbonates. It is evident that 1,1'-difluorodialkyl carbonates with different groups $R^1CHF$— and $R^2CHF$— can be produced if the aldehyde of formula (IV) in the reaction to produce fluoroformiates and the aldehyde of formula (III) reacted with the fluoroformiate of formula (II) in the subsequent step are different.

Thus, the compounds of formula (I) can be manufactured in a 2-step process comprising a step of preparing a fluoroformiate of formula (II), $R^1CHFOC(O)F$, from carbonyl fluoride and an aldehyde of formula (IV) $R^1CH(O)$ wherein $R^1$ denotes H or linear or branched alkyl with 1 to 3 C atoms; and a step of reacting the fluoroformiate of formula (II) with an aldehyde of formula (III), $R^2CH(O)$, wherein $R^2$ denotes H or linear or branched alkyl with 1 to 3 C atoms.

Preferred embodiments of the steps are those already described above, especially concerning the preferred use of a catalyst, using a formamide, especially dimethyl formamide, as preferred pre-catalyst in the first step, the pressure and temperature in the first and second step.

In an alternative to a 2-step way as described above, the compounds of formula (I) can be produced from $COF_2$ and the respective aldehyde in a 1-pot reaction. In a 1-pot process, the molar ratio of aldehyde to $COF_2$ is higher. Preferably, the molar ratio of aldehyde and $COF_2$ is equal to or greater than 1.8:1. Preferably, the molar ratio of aldehyde and $COF_2$ is equal to or lower than 10:1. A preferred range is from 1.8:1 to 3:1. A most preferred range for the molar ratio of the aldehyde and $COF_2$ is from 2:1 to 2.5:1. The 1-pot reaction is especially suitable for the manufacture of compounds o formula (I) where $R^1$ and $R^2$ are identical.

In such a 1-pot process, it is preferred to apply an acylation catalyst as mentioned above, e.g. dimethylaminopyridine.

The process of the invention provides selectively 1,1'-difluorodialkyl carbonates.

1,1'-difluorodiethyl carbonate exists in 2 diastereomers:

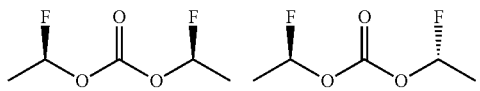

These 2 diastereomers have different boiling points and can be separated by distillation. The diastereomer on the left side of the drawing above is (R)-1-fluoroethyl-(S)-1'-fluorodiethyl carbonate. The diastereomer on the right side of the drawing above exists in 2 enantiomers, bis-(R)-1-fluoroethyl carbonate and bis-(S)-1-fluorodiethyl carbonate.

The isolated racemate and isolated (R)-1-(S)-1'-difluorodiethyl carbonate are novel and are further aspects of the present invention.

In the process of the present invention, a 1:1 racemate of the enantiomers is obtained.

The compounds of formula (I) can be used, as is described for example in US patent application publication 20090253044, as a solvent or as an additive for solvents in Li ion batteries.

Electrolyte solvents comprising isolated (R)-1-fluoroethyl-(S)-1'-fluoroethyl carbonate, and electrolyte solvents comprising isolated racemate of the 2 enantiomers, bis-(R)-1-fluoroethyl carbonate and bis-(S)-1-fluoroethyl carbonate, are another aspect of the present invention. The electrolyte solvents comprise >0% by weight, preferably equal to or more than 0.1% by weight of (R)-1-fluoroethyl-(S)-1'-fluoroethyl carbonate, or they comprise >0% by weight, preferably equal to or more than 0.1% by weight of the racemate of bis-(R)-1-fluoroethyl carbonate and bis-(S)-1-fluoroethyl carbonate. The electrolyte solvents comprise preferably equal to or less than 5% by weight of (R)-1-fluoroethyl-(S)-1'-fluoroethyl carbonate, or they comprise equal to or less than 5% by weight of the racemate of bis-(R)-1-fluoroethyl carbonate and bis-(S)-1-fluoroethyl carbonate. If the electrolyte solvent comprises both the racemate of bis-(R)-1-fluoroethyl carbonate and bis-(S)-1-fluoroethyl carbonate the compound (R)-1-fluoroethyl-(S)-1'-fluoroethyl carbonate, then either the molar ratio of bis-(R)-1-fluoroethyl carbonate and bis-(S)-1-fluoroethyl carbonate to (R)-1-fluoroethyl-(S)-1'-fluoroethyl carbonate is equal to or greater than 7:3, or it is equal to or lower than 3:7.

The respective electrolyte solvent comprising preferably 0.1 to 5% by weight of the racemate of bis-(R)-1-fluoroethyl carbonate and bis-(S)-1-fluoroethyl carbonate, or the compound (R)-1-fluoroethyl-(S)-1'-fluoroethyl carbonate, or mixtures of the racemate of bis-(R)-1-fluoroethyl carbonate and bis-(S)-1-fluoroethyl carbonate, or the compound (R)-1-fluoroethyl-(S)-1'-fluoroethyl carbonate e, respectively, with the proviso of the molar ratio given above, further comprises at least one further solvent useful in the field of electrolyte solutions for Li ion batteries. Preferably, the at least one solvent adds up to 100% by weight.

Suitable solvents (which generally are aprotic organic solvents) are known to the expert in the field of Li ion batteries. For example, organic carbonates, but also lactones, formamides, pyrrolidinones, oxazolidinones, nitroalkanes, N,N-substituted urethanes, sulfolane, dialkyl sulfoxides, dialkyl sulfites, acetates, nitriles, acetamides, glycol ethers, dioxolanes, dialkyloxyethanes, trifluoroacetamides, are very suitable.

Preferably, the aprotic organic solvent is selected from the group of dialkyl carbonates (which are linear) and alkylene carbonates (which are cyclic), and wherein the term "alkyl" denotes preferably C1 to C4 alkyl, the term "alkylene" denotes preferably C2 to C7 alkylene groups, including a vinylidene group, wherein the alkylene group preferably comprises a bridge of 2 carbon atoms between the oxygen atoms of the —O—C(O)—O— group; ketones, nitriles and formamides. Dimethyl formamide, carboxylic acid amides, for example, N,N-dimethyl acetamide and N,N-diethyl acetamide, acetone, acetonitrile, linear dialkyl carbonates, e.g. dimethyl carbonate, diethyl carbonate, methyl ethyl carbonate, cyclic alkylene carbonates, e.g. ethylene carbonate, propylene carbonate, and vinylidene carbonate, are suitable solvents.

Fluorosubstituted compounds different from the 1,1'-difluorodialkyl compounds mentioned above, for example, fluorinated carbonic esters which are selected from the group of fluorosubstituted ethylene carbonates, polyfluorosubstituted dimethyl carbonates, fluorosubstituted ethyl methyl carbonates, and fluorosubstituted diethyl carbonates are also suitable solvents. Preferred fluorosubstituted carbonates are monofluoroethylene carbonate, 4,4-difluoro ethylene carbonate, 4,5-difluoro ethylene carbonate, 4-fluoro-4-methyl ethylene carbonate, 4,5-difluoro-4-methyl ethylene carbonate, 4-fluoro-5-methyl ethylene carbonate, 4,4-difluoro-5-methyl ethylene carbonate, 4-(fluoromethyl)-ethylene carbonate, 4-(difluoromethyl)-ethylene carbonate, 4-(trifluoromethyl)-ethylene carbonate, 4-(fluoromethyl)-4-fluoro ethylene carbonate, 4-(fluoromethyl)-5-fluoro ethylene carbonate, 4-fluoro-4,5-dimethyl ethylene carbonate, 4,5-difluoro-4,5-dimethyl ethylene carbonate, and 4,4-difluoro-5,5-dimethyl ethylene carbonate; dimethyl carbonate derivatives including fluoromethyl methyl carbonate, difluoromethyl methyl carbonate, trifluoromethyl methyl carbonate, bis(difluoro)methyl carbonate, and bis(trifluoro)methyl carbonate; ethyl methyl carbonate derivatives including 2-fluoroethyl methyl carbonate, ethyl fluoromethyl carbonate, 2,2-difluoroethyl methyl carbonate, 2-fluoroethyl fluoromethyl carbonate, ethyl difluoromethyl carbonate, 2,2,2-trifluoroethyl methyl carbonate, 2,2-difluoroethyl fluoromethyl carbonate, 2-fluoroethyl difluoromethyl carbonate, and ethyl trifluoromethyl carbonate; and diethyl carbonate derivatives including ethyl (2-fluoroethyl) carbonate, ethyl (2,2-difluoroethyl) carbonate, bis(2-fluoroethyl) carbonate, ethyl (2,2,2-trifluoroethyl) carbonate, 2,2-difluoroethyl 2'-fluoroethyl carbonate, bis(2,2-difluoroethyl) carbonate, 2,2,2-trifluoroethyl 2'-fluoroethyl carbonate, 2,2,2-trifluoroethyl 2',2'-difluoroethyl carbonate, and bis(2,2,2-trifluoroethyl) carbonate, 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-fluoro-4,5-divinylethylene carbonate, 4,5-difluoro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate and 4,5-difluoro-4,5-diphenylethylene carbonate, fluoromethyl phenyl carbonate, 2-fluoroethyl phenyl carbonate, 2,2-difluoroethyl phenyl carbonate and 2,2,2-trifluoroethyl phenyl carbonate, fluoromethyl vinyl carbonate, 2-fluoroethyl vinyl carbonate, 2,2-difluoroethyl vinyl carbonate and 2,2,2-trifluoroethyl vinyl carbonate, fluoromethyl allyl carbonate, 2-fluoroethyl allyl carbonate, 2,2-difluoroethyl allyl carbonate and 2,2,2-trifluoroethyl allyl carbonate are mentioned as suitable components of electrolyte solutions of the invention.

Other suitable components of solvents according to the present invention are those described in WO2007/042471 selected from the group of aromatic compounds consisting of 1-acetoxy-2-fluorobenzene, 1-acetoxy-3-fluorobenzene, 1-acetoxy-4-fluorobenzene, 2-acetoxy-5-fluorobenzyl acetate, 4-acetyl-2,2-difluoro-1,3-benzodioxole, 6-acetyl-2,2,3,3-tetrafluorobenzo-1,4-dioxin, 1-acetyl-3-trifluoromethyl-5-phenylpyrazole, 1-acetyl-5-trifluoromethyl-3-phenylpyrazole, benzotrifluoride, benzoyltrifluoroacetone, 1-benzoyl-3-trifluoromethyl-5-methylpyrazole, 1-benzoyl-5-trifluoromethyl-3-methylpyrazole, 1-benzoyloxy-4-(2,2,2-trifluoroethoxy)benzene, 1-benzoyl-4-trifluoromethylbenzene, 1,4-bis(t-butoxy)tetrafluorobenzene, 2,2-bis(4-methylphenyl)hexafluoropropane, bis(pentafluorophenyl) carbonate, 1,4-bis(1,1,2,2-tetrafluoroethoxy)benzene, 2,4-bis(trifluoromethyl)benzaldehyde, 2,6-bis(trifluoromethyl) benzonitrile, difluoroacetophenone, 2,2-difluorobenzodioxole, 2,2-difluoro-1,3-benzodioxole-4-carbaldehyde, 1-[4-(difluoromethoxy)phenyl]ethanone, 3-(3,5-difluorophenyl)-1-propene, fluorobenzophenone, difluorobenzophenone, 1-(2'-fluoro[1,1'-biphenyl]-4-yl)propan-1-one, 6-fluoro-3,4-dihydro-2H-1-benzothiin-4-one, 4-fluorodiphenyl ether, 5-fluoro-1-indanone, 1-(3-fluoro-4-methoxyphenyl)ethanone, fluorophenylacetonitrile, the group of compounds having an Si—C bond consisting of bis(pentafluorophenyl) dimethylsilane, 1,2-bis[difluoro(methyl)silyl]ethane, N,O-bis(trimethylsilyl)trifluoroacetamide, N-(t-butyldimethylsilyl)-N-methyltrifluoroacetamide, t-butyldimethylsilyl trifluoromethanesulphonate, 2-dimethylamino-1,3-dimethylimidazolium trimethyldifluorosiliconate, diphenyldifluorosilane, the group of compounds having a C=O bond consisting of bis(1,1,1,3,3,3-hexafluoroprop-2-yl) 2-methylenesuccinate, bis(1,1,1,3,3,3-hexafluoroprop-2-yl) maleate, bis(2,2,2-trifluoroethyl) maleate, bis(perfluorooctyl) fumarate, bis(perfluoroisopropyl) ketone, 2,6-bis(2,2,2-trifluoroacetyl)cyclohexanone, butyl 2,2-difluoroacetate, cyclopropyl 4-fluorophenyl ketone, diethyl perfluoroadipate, N,N-diethyl-2,3,3,3-tetrafluoropropionamide, the group of compounds having a C=C bond consisting of allyl 1H,1H-heptafluorobutyl ether, trans-1,2-bis(perfluorohexyl)ethylene, (E)-5,6-difluoroocta-3,7-diene-2-one, the group of amines consisting of N,N-diethyl-1,1,2,3,3,3-hexafluoropropylamine.

These compounds are applicable as additive or additives for electrolyte solvents in Li ion batteries, Li-sulfur batteries and lithium-air batteries. The solvent may also additionally contain benzene, fluorobenzene, toluene, trifluorotoluene, xylene or cyclohexane.

The term "difluoroacetophenone" encompasses the isomers with the fluorine substitution in the 2,3-, 2,4-, 2,5-, 2,6-, 3,4- and 3,5-position on the aromatic ring.

The term "fluorobenzophenone" encompasses in particular the isomers 2-fluorobenzophenone and 4-fluorobenzophenone.

The term "difluorobenzophenone" encompasses the isomers with the fluorine substitution in the 2,3'-, 2,3-, 2,4'-, 2,4-, 2,5-, 2,6-, 3,3'-, 3,4'-, 3,4-, 3,5- and 4,4'-position.

The term "fluorophenylacetonitrile" encompasses the isomers with the fluorine substitution in the 2-, 3- and 4-position.

The compounds can be synthesized in a known manner and are also commercially available, for example from ABCR GmbH & Co. KG, Karlsruhe, Germany.

Preferred fluorinated organic compounds are selected from the group of fluorosubstituted carboxylic acid esters, fluorosubstituted carboxylic acid amides, fluorosubstituted fluorinated ethers, fluorosubstituted carbamates, fluorosubstituted cyclic carbonates, fluorosubstituted acyclic carbonates, fluorosubstituted phosphites, fluorosubstituted phosphoranes, fluorosubstituted phosphoric acid esters, fluorosubstituted phosphonic acid esters and saturated or unsaturated fluorosubstituted heterocycles.

Suitable fluorinated ethers applicable as solvent or solvent additive are for example those as described in U.S. Pat. No. 5,916,708, namely partially fluorinated ethers of formula (I)

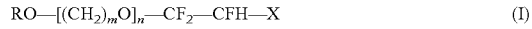

wherein
R is a linear alkyl group with 1 to 10 C atoms or a branched alkyl group with 3 to 10 C atoms,
X is fluorine, chlorine or a perfluoroalkyl group with 1 to 6 C atoms which groups may include ether oxygen,
m is an integer of 2 to 6 and
n is an integer of 1 to 8,
and/or of formula (II)

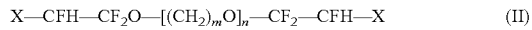

wherein
X, m and n have the meaning given above.

Partially fluorinated carbamates suitable as solvent additives are for example those described in U.S. Pat. No. 6,159,640, namely compounds of the formula $R^1R^2N$—C(O)$OR^3$ wherein $R^1$ and $R^2$ independently are the same or different, and are linear C1-C6-alkyl, branched C3-C6-alkyl, C3-C7-cycloalkyl, or $R^1$ and $R^2$ are connected directly or via one or more additional N and/or O atoms forming a ring with 3 to 7 members. Optionally, additional N atoms in the ring are saturated with C1 to C3 alkyl groups, and additionally, the carbon atoms of the ring may be substituted by C1 to C3 alkyl groups. In the groups $R^1$ and $R^2$, one or more hydrogen atoms may be substituted by fluorine atoms. $R^3$ is a partially fluorinated or perfluorinated linear or branched alkyl group with 1 to 6 or, respectively, 3 to 6 carbon atoms, or a partially or perfluorinated cycloalkyl group with 3 to 7 C atoms, which may be substituted by one or more C1 to C6 alkyl groups.

Fluorinated acetamides suitable as solvent additive are for example those described U.S. Pat. No. 6,489,064, namely partially fluorinated amide corresponding to formula $R^1CO\text{---}NR^2R^3$ (III) wherein $R^1$ is a linear C1-C6 alkyl group in which at least one hydrogen atom is replaced by fluorine, or a branched C3-C6 alkyl group in which at least one hydrogen atom is replaced by fluorine, or a C3-C7 cycloalkyl group optionally substituted one or more times by a linear C1-C6 alkyl group or branched C3-C6 alkyl group or both in which at least one hydrogen atom of the cycloalkyl group or the optional linear or branched alkyl substituent or both is replaced by fluorine, and $R^2$ and $R^3$ independently represent an identical or different linear C1-C6 alkyl group, a branched C3-C6 alkyl group or a C3-C7 cycloalkyl group, or together with the amide nitrogen form a saturated five or six-membered nitrogen-containing ring, or are joined with one or more additional N and/or O atom(s) to form a 4 to 7-membered ring in which the additional N atoms present in the ring are optionally saturated with C1-C3 alkyl groups and the ring carbon atoms may also carry C1-C3 alkyl groups.

Partially fluorinated esters suitable as solvent or solvent additive are for example those described in U.S. Pat. No. 6,677,085 partially fluorinated compound derived from a diol corresponding to formula (IV):$R^1CO\text{---}O\text{---}[CHR^3(CH_2)_m\text{---}O]_n\text{---}R^2$ (IV) wherein $R^1$ is a (C1-C8) alkyl group or a (C3-C8) cycloalkyl group, wherein each of said groups is partially fluorinated or perfluorinated so that at least one hydrogen atom of the group is replaced by fluorine; $R^2$ is a (C1-C8) alkyl carbonyl or (C3-C8) cycloalkyl carbonyl group, wherein said alkylcarbonyl or cycloalkylcarbonyl group may optionally be partially fluorinated or perfluorinated; $R^3$ is a hydrogen atom or a (C1-C8) alkyl or (C3-C8) cycloalkyl group; m is 0, 1, 2 or 3, and n is 1, 2 or 3.

Another aspect of the present invention is an electrolyte composition comprising a solvent as mentioned above and at least one dissolved electrolyte salt. Such salts have the general formula $M_aA_b$. M is a metal cation, and A is an anion. The overall charge of the salt $M_aA_b$ is 0. M is preferably selected from $Li^+$ and $NR_4^+$. Preferred anions are $PF_6^-$, $PO_2F_2^-$, $AsF_6^-$, $BF_4^-$, $ClO_4^-$, $N(CF_3SO_2)_2^-$ and $N(i\text{-}C_3F_7SO_2)_2^-$ all of which have 1 negative charge.

Preferably, M is $Li^+$. Especially preferably, M is $Li^+$ and the solution comprises at least one electrolyte salt selected from the group consisting of $LiBF_4$, $LiClO_4$, $LiAsF_6$, $LiPF_6$, $LiPO_2F_2$, $LiN(CF_3SO_2)_2$ and $LiN(i\text{-}C_3F_7SO_2)_2$. Lithium bis(oxalato)borate can be applied as an additional additive. The concentration of the electrolyte salt is preferably 1±0.1 molar. Often, the electrolyte composition may comprise $LiPF_6$ and $LiPO_2F_2$.

If $LiPO_2F_2$ is the only electrolyte salt, its concentration in the electrolyte composition is, as mentioned, preferably 1±0.1 molar. If $LiPO_2F_2$ is applied as an additive together with another electrolyte salt, especially together with $LiPF_6$, the concentration of $LiPO_2F_2$ in the electrolyte composition preferably is equal to or greater than 0.1% by weight, more preferably equal to or greater than 0.5% by weight; preferably, its concentration is equal to or lower than 10% by weight, more preferably, equal to or lower than 5% by weight when the total electrolyte composition including electrolyte salt, solvent and additives is set as 100% by weight.

Should the disclosure of any patents, patent applications, and publications which are incorporated herein by reference conflict with the description of the present application to the extent that it may render a term unclear, the present description shall take precedence.

The invention will now be further described in examples without intending to limit it.
Abbreviations
DMAP=2-dimethylaminopyridine

EXAMPLE 1: PREPARATION OF 1,1'-DIFLUOROETHYL CARBONATE 1.1 Preparation of 1-fluoroethyl fluoroformiate
1-fluoroethyl fluoroformiate is prepared as described in example 3 of WO 2011006822:

Acetaldehyde (12 g; 272 mmol) and dimethylformamide (200 mg; 71 mmol) were given into an autoclave with an internal volume of about 40 ml. The autoclave was closed, evacuated and pressurized to about 5 bar (abs.) with dry nitrogen and evacuated again. Then, carbonyl fluoride (18 g; 272 mmol) was given into the autoclave over a period of 30 min. The mixture was stirred at room temperature for 30 min after which the pressure fell from 20 bar to 0 bar. The autoclave was then pressurized two times with nitrogen, each time up to a pressure of about 5 bar (abs.).

If desired, 1-fluoroethyl fluoroformiate formed can be isolated by distillation.
1.2. Preparation of 1,1'-difluoroethyl carbonate Into a 250 mL PFA-flask equipped with a reflux condenser (cooling media were kept at −20° C.), 50 g of 1-fluoroethyl fluoroformiate were added to 30 g of acetaldehyde and 0.25 g DMAP at 0° C. under an inert atmosphere. After 8 h of stirring at room temperature, 0.1 g of DMAP was added. After stirring for additional 16 h, another 0.1 g of DMAP was added. The mixture was stirred for additional 24 h. To the resulting reaction mixture, 25 g water were added. After stirring for 5 minutes, the resulting two phases were separated. The organic phase was washed with water (2×10 mL) and dried over $Na_2SO_4$. The product was obtained as a colourless liquid (59.5 g) in a purity of 88.5% (GC, two diastereomers).

If desired, the product can be purified by distillation. During distillation, it is possible to separate the diastereomers.

EXAMPLE 2: ELECTROLYTE SOLVENT COMPRISING THE RACEMATE OF 1,1'-DIFLUORODIETHYL CARBONATE

Propylene carbonate, ethylene carbonate and the racemate of 1,1'-difluorodiethyl carbonate are mixed in a volume ratio of 48:48:2 to provide an electrolyte solvent suitable for Li ion batteries.

EXAMPLE 3: ELECTROLYTE COMPOSITION COMPRISING $LIPF_6$

To the electrolyte solvent of example 1, $LiPF_6$ is added in a glove box under inert gas such that the concentration of $LiPF_6$ is 1-molar to obtain an electrolyte composition suitable for Li ion batteries.

EXAMPLE 4: ELECTROLYTE SOLVENT COMPRISING A MIXTURE OF

Propylene carbonate, ethylene carbonate and the racemate of 1-fluoroethyl-1'-fluorodiethyl carbonate are mixed in a volume ratio of 48:48:2 to provide an electrolyte solvent suitable for Li ion batteries.

EXAMPLE 5: ELECTROLYTE COMPOSITION COMPRISING LIPF$_6$

To the electrolyte solvent of example 1, LiPF$_6$ is added in a glove box under inert gas such that the concentration of LiPF$_6$ is 1-molar to obtain an electrolyte composition suitable for Li ion batteries.

EXAMPLE 6: ELECTROLYTE COMPOSITIONS COMPRISING LIPF$_6$ AS ELECTROLYTE SALT

Electrolyte compositions can be produced using the mixture of (R)-1-fluoroethyl-(S)-1'fluoroethyl carbonate, bis-(R)-1-fluoroethyl carbonate and bis-(S)-1-fluoroethyl carbonate (as obtained during the manufacture without separation of the isomers); or of mixtures of bis-(R)-1-fluoroethyl carbonate and bis-(S)-1-fluoroethyl carbonate; or of (R)-1-fluoroethyl-(S)-1'fluoroethyl carbonate with other electrolyte solvents. In the following table, electrolyte compositions are presented using the racemate of 1-fluoroethyl-1'-fluoroethyl carbonate

| Compound of formula (I); amount [% by weight] | Solvent [balance to 100 % by weight] | Electrolyte salt; amount [mol/l] | Further additive; amount [% by weight] |
|---|---|---|---|
| 1,1'-DFDC*; 2 | EC** | 1 | — |
| 1,1'-DFDC; 3 | EC | 1 | — |
| 1,1'-DFDC; 4 | EC | 1 | — |
| 1,1'-DFDC; 3 | EC/PC*** vol/vol 1:1 | 1 | F1EC****; 2 |
| 1,1'-DFDC; 3 | EC/PC vol/vol 1:1 | 1 | LiPOF*****; 1 |
| 1,1'-DFDC; 3 | EC/PC vol/vol 1:1 | 1 | — |
| 1,1'-DFDC; 3 | EC/DMC****** vol/vol 1:1 | 1 | F1EC; 2 |
| 1,1'-DFDC; 3 | EC/DMC vol/vol 1:1 | 1 | LiPOF; 1 |
| 1,1'-DFDC; 3 | EC/DMC vol/vol 1:1 | 1 | — |
| 1,1'-DFDC; 3 | DMC | 1 | — |
| Bis-(R)-1,1'-DFDC/Bis-(S)-1,1'-DFDC; 3 | DMC | 1 | — |
| (R)-1-(S)-1'-DFDC; 3 | DMC | 1 | — |

*1,1'-DDFC = 1-fluoroethyl-1'-fluoroethyl carbonate (racemate)
**EC = Ethylene carbonate
***PC = Propylene carbonate
****F1EC = monofluoroethylene carbonate
*****LiPOF = LiPO$_2$F$_2$
******DMC = Dimethyl carbonate The electrolyte compositions are prepared by mixing appropriate amounts of 1,1'-difluoroethyl carbonate, the solvent or solvents, the electrolyte salt and additives if applied in a vessel which is dried beforehand and through which dry N$_2$ is passed to prevent an atmosphere which is dry and free of oxygen.

The invention claimed is:

1. A process for the manufacture of 1,1'-difluorodialkyl carbonates of the general formula (I), R$^1$CHF—OC(O)—OCHFR$^2$, wherein R$^1$ and R$^2$ are the same or different and denote H or linear or branched alkyl with 1 to 3 C atoms, the process comprising reacting a fluoroformiate of formula (II), R$^1$CHFOC(O)F wherein R$^1$ has the meaning given above, with an aldehyde of formula (III), R$^2$—CH(O) wherein R$^2$ has the meaning given above; wherein the reaction of the fluoroformiate of formula (II) and the aldehyde of formula (III) is performed at a temperature from 0° C. to room temperature in the presence of an acylation catalyst, which is pyridine or a substituted pyridine compound.

2. The process of claim 1 wherein R$^1$ is H or CH$_3$.

3. The process of claim 1 wherein R$^2$ is H or CH$_3$.

4. The process of claim 2 wherein CH$_2$F—OC(O)—OCH$_2$F or CH$_3$CHF—OC(O)—OCHFCH$_3$ are produced.

5. The process of claim 1 wherein the molar ratio between the fluoroformiate of formula (II) and the aldehyde of formula (III) is from 0.9:1 to 5:1.

6. The process of claim 1 wherein the fluoroformiate of formula (II) is prepared from carbonyl fluoride and an aldehyde of formula (IV) R$^1$CH(O) wherein R$^1$ has the meaning given above.

7. The process of claim 6 wherein the 1,1'-difluorodialkyl carbonate is manufactured from carbonyl fluoride and the aldehyde of formula (IV) in a 1-pot reaction.

8. The process of claim 6 wherein the reaction is performed in the presence of an acylation catalyst.

9. The process of claim 1 wherein the reaction of the fluoroformiate of formula (II) and the aldehyde of formula (III) is performed at a temperature from equal to or higher than 20° C.

10. The process of claim 1 wherein the acylation catalyst is 4-dimethylaminopyridine.

11. The process of claim 1 wherein the reaction of the fluoroformiate of formula (II) and the aldehyde of formula (III) is performed at a temperature from 0° C. to 20° C.

* * * * *